(12) United States Patent
Lee et al.

(10) Patent No.: US 8,038,620 B2
(45) Date of Patent: Oct. 18, 2011

(54) FRESNEL ZONE IMAGING SYSTEM AND METHOD

(75) Inventors: Warren Lee, Clifton Park, NY (US); Kenneth Wayne Rigby, Clifton Park, NY (US); Lowell Scott Smith, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1609 days.

(21) Appl. No.: 11/313,449

(22) Filed: Dec. 20, 2005

(65) Prior Publication Data

US 2007/0167786 A1 Jul. 19, 2007

(51) Int. Cl.
*A61B 8/00* (2006.01)
*G01S 15/00* (2006.01)

(52) U.S. Cl. ........... 600/447; 367/105
(58) Field of Classification Search .......... 600/437, 600/459, 443–447; 310/334, 336, 314–317; 367/7, 11, 178, 103–105, 121–123, 137–138, 367/174

See application file for complete search history.

(56) References Cited

U.S. PATENT DOCUMENTS

| | | | | |
|---|---|---|---|---|
| 3,911,730 A * | 10/1975 | Niklas | | 73/624 |
| 4,112,411 A * | 9/1978 | Alais et al. | | 367/135 |
| 4,117,446 A | 9/1978 | Alais | | |
| 4,119,938 A | 10/1978 | Alais | | |
| 4,228,686 A * | 10/1980 | Tancrell | | 73/626 |
| 4,677,981 A * | 7/1987 | Coursant | | 600/447 |
| 5,060,651 A * | 10/1991 | Kondo et al. | | 600/443 |
| 5,396,143 A * | 3/1995 | Seyed-Bolorforosh et al. | | 310/334 |
| 5,651,365 A * | 7/1997 | Hanafy et al. | | 600/459 |
| 5,882,309 A * | 3/1999 | Chiao et al. | | 600/459 |
| 6,066,099 A * | 5/2000 | Thomenius et al. | | 600/447 |
| 6,271,620 B1* | 8/2001 | Ladabaum | | 310/334 |
| 6,381,197 B1* | 4/2002 | Savord et al. | | 367/178 |
| 6,551,246 B1* | 4/2003 | Ustuner et al. | | 600/447 |
| 6,726,631 B2* | 4/2004 | Hatangadi et al. | | 600/459 |
| 7,087,023 B2* | 8/2006 | Daft et al. | | 600/459 |
| 7,107,825 B2* | 9/2006 | Degertekin et al. | | 73/105 |
| 7,293,462 B2* | 11/2007 | Lee et al. | | 73/649 |
| 7,549,962 B2* | 6/2009 | Dreschel et al. | | 600/443 |
| 2002/0042577 A1* | 4/2002 | Hatangadi et al. | | 600/459 |
| 2004/0160144 A1* | 8/2004 | Daft et al. | | 310/334 |
| 2005/0124882 A1* | 6/2005 | Ladabaum et al. | | 600/437 |
| 2007/0079658 A1* | 4/2007 | Wagner | | 73/627 |

OTHER PUBLICATIONS

Chris Daft et al., "Elevation Beam Profile Control With Bias Polarity Patterns Applied to Microfabricated Ultrasound Transducers", 2003 IEEE International Ultrasonics Symposium Proceedings, pp. 4.

* cited by examiner

*Primary Examiner* — Francis Jaworski
(74) *Attorney, Agent, or Firm* — Joseph J. Christian

(57) ABSTRACT

A method for Fresnel zone imaging is provided. The method comprises identifying a plurality of constructive regions and a plurality of destructive regions in an energy transmitting device and converting the destructive regions to the constructive regions by using an apodization profile. The apodization profile comprises apodization values for each constructive region and destructive region and the apodization values comprise real numbers.

9 Claims, 11 Drawing Sheets

FRESNEL ZONE IMAGING SYSTEM AND METHOD

BACKGROUND

The present invention relates generally to imaging systems, and specifically to Fresnel zone imaging methods in ultrasound imaging systems.

Ultrasound imaging is usually achieved through the use of a transducer array, which is composed of multiple individually addressable elements that are activated in such a way as to form an acoustic beam (beamforming). The beam is of a certain shape and is directed towards specific locations in the imaging medium that suit the particular imaging configuration. The transducer array receives back scattered signals from the imaging medium which are then used to create an ultrasound image.

In most imaging applications, image quality is an important parameter. Typically, image quality metrics include spatial resolution and contrast resolution. Image quality, including resolution and contrast, is directly related to the acoustic beam characteristics. Characteristics of the acoustic beam are in turn determined by the physical properties of the transducer array, the imager's transmit and receive electronics, as well as the electronic phasing or time delays applied to the array elements.

It is desirable to confine the acoustic beam to as small a spatial region as possible. Sidelobes are regions around the main beam where significant acoustic energy is both propagated and sensed. Sidelobes are usually undesirable as they reduce both image resolution and contrast.

Specifically, in Fresnel zone imaging, a transducer can be divided into regions or zones that contribute either constructively or destructively to the focus point, based on the geometric propagation distance between the focus point and the specific point on the transducer being considered. The Fresnel zones simplify the system hardware in two ways. Firstly, it allows larger groupings of elements to use a single time delay. In other words, all the elements within a given zone share the same delay rather than independent time delays for each element. Secondly, especially in optical or similar narrow-band systems, one specific time delay for all constructive zones is used and a different time delay is used for all destructive zones.

In Fresnel zone imaging with cMUT or electrostrictive elements, regions of destructive interference can be converted to regions of constructive interference by applying an apodization profile consisting of discrete, relative apodization weights of −1 and +1 to the destructive and constructive regions respectively. One problem with the above described method in which the weighting of the various regions of the transducer is restricted to the values +1 and −1 is the generation of radiation patterns with a certain sidelobe level.

Accordingly, there is a need to generate a weighting pattern that minimizes the generation of sidelobes while using Fresnel zone imaging techniques.

BRIEF DESCRIPTION

Briefly, according to one embodiment of the invention, a method for Fresnel zone imaging is provided. The method comprises identifying a plurality of constructive regions and a plurality of destructive regions in an energy transmitting device and converting the destructive regions to constructive regions by using an apodization profile. The apodization profile comprises apodization values for each constructive region and destructive region and the apodization values comprise real numbers.

In an alternate embodiment, an ultrasound imaging system comprises a transducer array comprising a plurality of transducers, the array being configured to focus an ultrasound beam on a region of interest; each transducer comprising a plurality of constructive regions and a plurality of destructive regions. The system further includes a processor configured to generate an apodization profile. The apodization profile comprises apodization values for each constructive region and destructive region and the apodization values comprise real numbers. The system also includes a control system configured to apply a bias voltage to each transducer region. The bias voltage is derived using the apodization profile.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
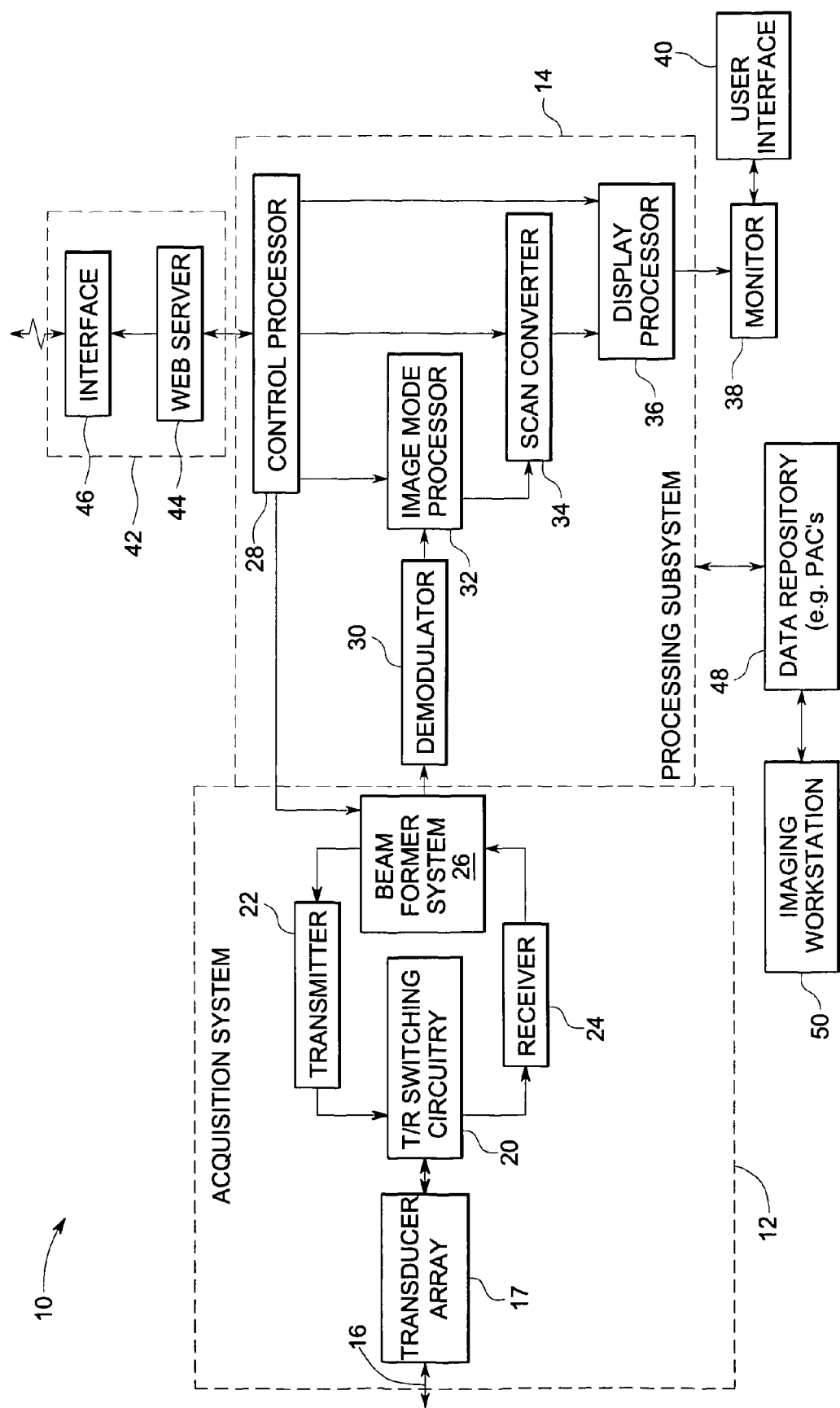
FIG. 1 is a block diagram of one embodiment of an ultrasound imaging system implementing a Fresnel zone imaging technique.

FIG. 1 is a block diagram of an embodiment of an ultrasound system 10 using Fresnel zone imaging methods. It may be appreciated that the ultrasound system of FIG. 1 is shown by way of example only. Fresnel zone imaging techniques may also be used in other imaging systems such as radar systems, sonar systems and optical systems.

The ultrasound system comprises acquisition subsystem 12 and processing subsystem 14. The acquisition subsystem 12 comprises an energy transmitting device, transmit/receive switching circuitry 20, a transmitter 22, a receiver 24, and a beamformer 26. Fresnel zone imaging is used in the acquisition subsystem that enables the focussing of the ultrasound beam in a desired direction. In the illustrated embodiment, the energy transmitting device is a transducer array 17 composed of a plurality of transducer elements 17-1 through 17-M.

Processing subsystem 14 comprises a control processor 28, a demodulator 30, an imaging mode processor 32, a scan converter 34 and a display processor 36. The display processor is further coupled to a monitor for displaying images. An operator may interact with the control processor and the display monitor via user interface 40. The control processor may also be coupled to a remote connectivity subsystem 42 comprising a web server 44 and a remote connectivity interface 46. Processing subsystem may be further coupled to data repository 48 to receive ultrasound image data. The data repository interacts with image workstation 50.

The architectures and modules may be dedicated hardware elements such as circuit boards with digital signal processors or may be software running on a general purpose computer or processor such as a commercial, off-the-shelf PC. The various architectures and modules may be combined or separated according to various embodiments of the invention.

Figure 2:
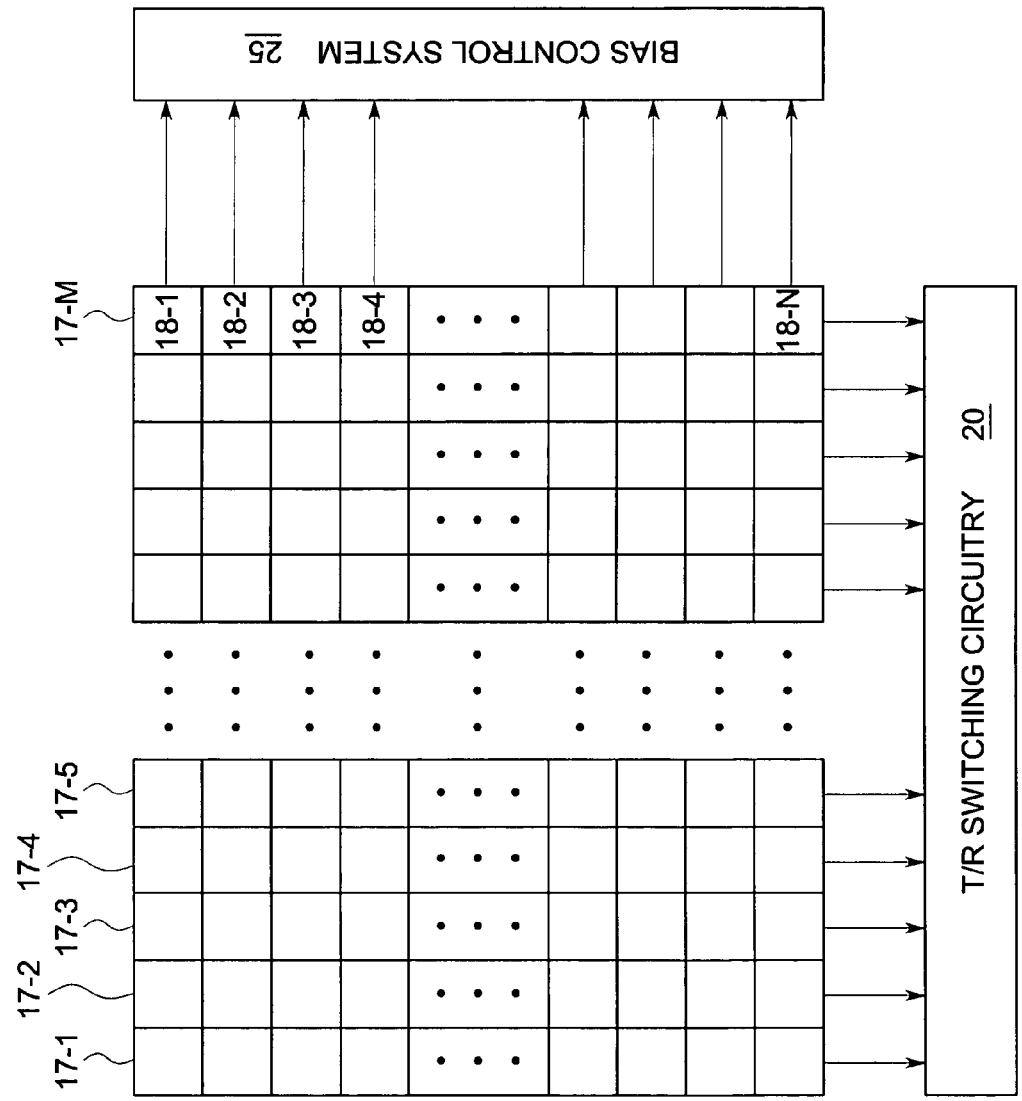
FIG. 2 is a block diagram of a transducer array implemented according to one aspect of the invention.

In the acquisition subsystem 12, a transducer array 17 (comprising a plurality of transducer array elements 17-1 through 17-M) is in contact with a subject (not shown). FIG. 2 is a block diagram of a detailed view of a transducer array. The transducer array comprises elements 17-1 through 17-M, where 'M' is an integer. Each transducer element 17-1 through 17-M includes transducer element regions 18-1 through 18-N, where 'N' is an integer. Each element is coupled to transmit/receive switching circuitry 20 and each region 18-1 through 18-N is coupled to a bias control system 25. In a specific embodiment, the transducer array comprises capacitive micromachined ultrasound transducers (cMUTs).

Continuing with FIG. 1, the transducer array is coupled to the transmit/receive (T/R) switching circuitry 20. The T/R switching circuitry 20 is coupled to the output of transmitter 22 and the input of receiver 24. The output of receiver 24 is an input to beamformer 26. Beamformer 26 is further coupled to the input of transmitter 22, and to the input of demodulator 30. The beam former 26 is also coupled to the control processor 28.

In processing subsystem 14, the output of demodulator 30 is coupled to an input of imaging mode processor 32. Control processor interfaces to imaging mode processor 32, scan converter 34 and to display processor 36. An output of imaging mode processor 32 is coupled to an input of scan converter 34. An output of scan converter 34 is coupled to an input of display processor 36. The output of display processor 36 is coupled to monitor 38.

Transducer array 17 transmits ultrasound energy into subject and receives and processes backscattered ultrasound signals 16 from the subject to create and display an image. To generate a transmitted beam of ultrasound energy, the control processor 28 sends command data to the beamformer 26 to generate transmit parameters to create a beam of a desired shape originating from a certain point at the surface of the transducer array 17 at a desired steering angle. The transmit parameters are sent from the beamformer 26 to the transmitter 22. The transmitter 22 uses the transmit parameters to properly encode transmit signals to be sent to the transducer array 17 through the T/R switching circuitry 20. The transmit signals are set at certain levels and phases with respect to each other and are provided to individual transducer elements of the transducer array 17. The transmit signals excite the transducer elements to emit ultrasound waves with the same phase and level relationships as those in the transmit signals. As a result, a transmitted beam of ultrasound energy is formed in a subject within a scan plane along a scan line when the transducer array 17 is acoustically coupled to the subject by using, for example, ultrasound gel. Electronic scanning is achieved by the sequential generation of beams directed along different lines within the subject.

The transducer array 17 is a two-way transducer. When ultrasound waves are transmitted into a subject, the ultrasound waves are backscattered off the tissue and blood samples within the structure. The transducer array 17 receives the backscattered waves at different times, depending on the echo propagation distance in the tissue. The transducer elements are responsive to the backscattered waves and convert the ultrasound energy from the backscattered waves into electrical signals.

The received electrical signals are routed through the T/R switching circuitry 20 to the receiver 24. The receiver 24 amplifies and digitizes the received signals and provides other functions such as gain compensation. The digitized received signals correspond to the backscattered waves received by each transducer element at various times and preserve the amplitude and phase information of the backscattered waves.

The digitized received signals are sent to beamformer 26. The control processor 28 sends command data to beamformer 26. Beamformer 26 uses the command data to form a receive beam originating from a point on the surface of transducer array 17 at a steering angle typically corresponding to the point and steering angle of the previous ultrasound beam transmitted along a scan line. The beamformer 26 operates on the appropriate received signals by performing time delaying and summing, according to the instructions of the command data from the control processor 28, to create received beam signals corresponding to sample volumes along a scan line in the scan plane within the subject. The phase, amplitude, and timing information of the received signals from the various transducer elements is used to create the received beam signals.

The received beam signals are sent to processing subsystem 14. Demodulator 30 demodulates the received beam signals to create pairs of I and Q demodulated data values corresponding to sample volumes within the scan plane. Demodulation is accomplished by comparing the phase and amplitude of the received beam signals to a reference frequency. The I and Q demodulated data values preserve the phase and amplitude information of the received signals.

The demodulated data is transferred to imaging mode processor 32. Imaging mode processor 32 uses parameter estimation techniques to generate imaging parameter values from the demodulated data in scan sequence format. The imaging parameters may comprise parameters corresponding to various possible imaging modes such as, for example, B-mode, color velocity mode, spectral Doppler mode, and tissue velocity imaging mode. The imaging parameter values are passed to scan converter 34. Scan converter 34 processes the parameter data by performing a translation from scan sequence format to display format. The translation includes performing interpolation operations on the parameter data to create display pixel data in the display format.

The scan converted pixel data is sent to display processor 36 to perform any final spatial or temporal filtering of the scan converted pixel data, to apply grayscale or color to the scan converted pixel data, and to convert the digital pixel data to analog data for display on monitor 38. The user interface 40 interacts with the control processor 28 based on the data displayed on monitor 38.

Figure 3:
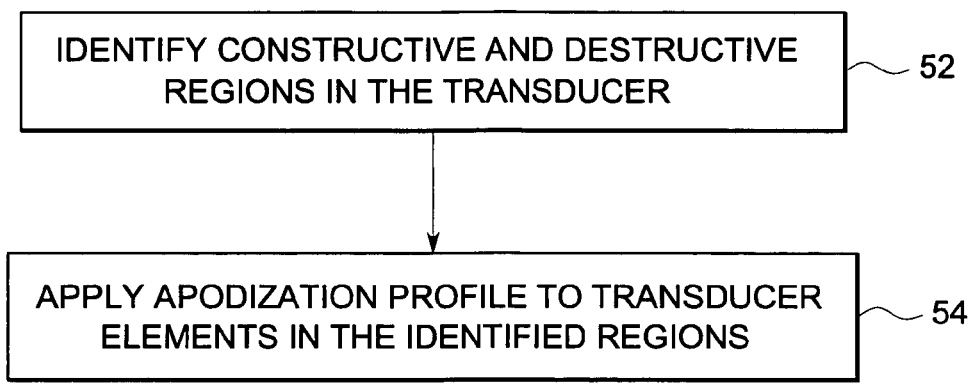
FIG. 3 is a flow chart illustrating one method for Fresnel zone imaging according to one aspect of the invention.

FIG. 3 is a flow chart illustrating one method for Fresnel zone imaging according to one aspect of the invention. In step 52, constructive regions and destructive regions on the transducer array are identified. These regions are described relative to a Fresnel reference point, typically the center of the array. Constructive regions refer to those regions on the transducer array where the propagation distance to the focus point differs from the propagation distance between the Fresnel reference point on the array and the focus point by approximately integer multiples of a wavelength. Similarly, destructive regions refer to those regions on the transducer array where the propagation distance to the focus point differs from propagation distance between the Fresnel reference point and the focus point by odd integer multiples of half wavelengths.

Figure 4:
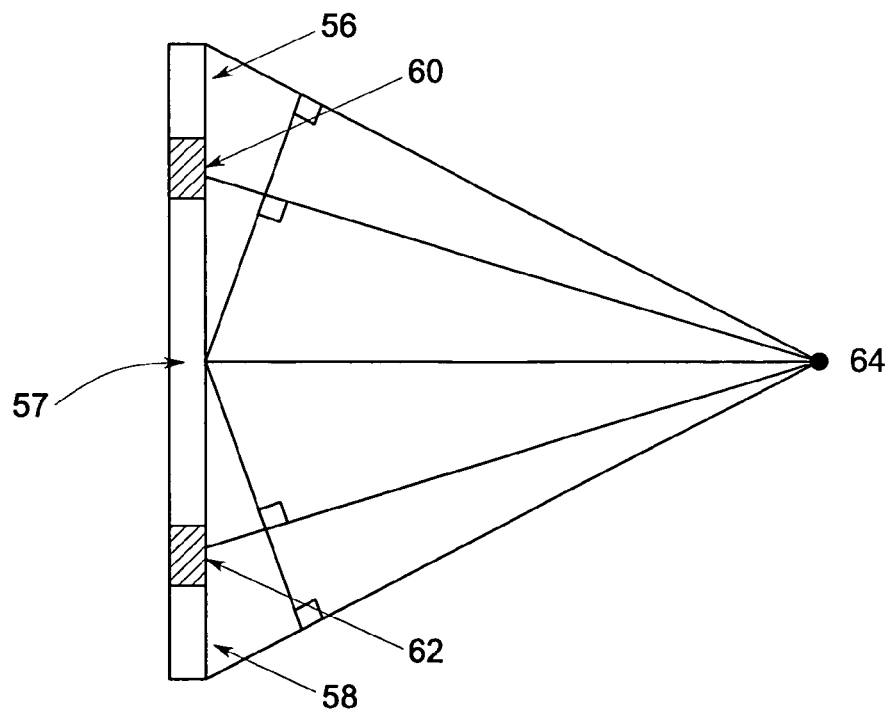
FIG. 4 is a diagrammatic view of constructive regions and destructive regions in transducer array.

FIG. 4 is a diagrammatic view of one embodiment of a transducer element with constructive regions and destructive regions. Transducer array 17 comprises elements with constructive regions 56, 57 and 58 and destructive regions 60 and 62 respectively.

Continuing with FIG. 3, in step 54, an apodization profile is applied to the identified regions to convert the destructive regions on the transducer array to constructive regions by using an apodization profile. The apodization profile includes apodization values for each constructive region and destructive region. The apodization values comprise real numbers. The apodization profile in elevation depends on the frequency of operation, the focal zone, and the geometry of the transducer. In one embodiment, the apodization values are varied dynamically in order to form an image with multiple elevation foci.

In one embodiment, the apodization values comprise the numbers −1 and +1. Constructive regions are assigned the value −1 and destructive regions are assigned the value +1. It will be appreciated that this choice of assignment is arbitrary and that constructive and destructive regions can be assigned any apodization values with opposite signs.

In a more specific embodiment, transition regions are identified on the transducer array. Transition regions are defined as regions on the transducer array, which lie between the constructive regions, and the destructive regions. In a more specific embodiment, the transition regions are assigned an apodization value of zero.

Figure 5:
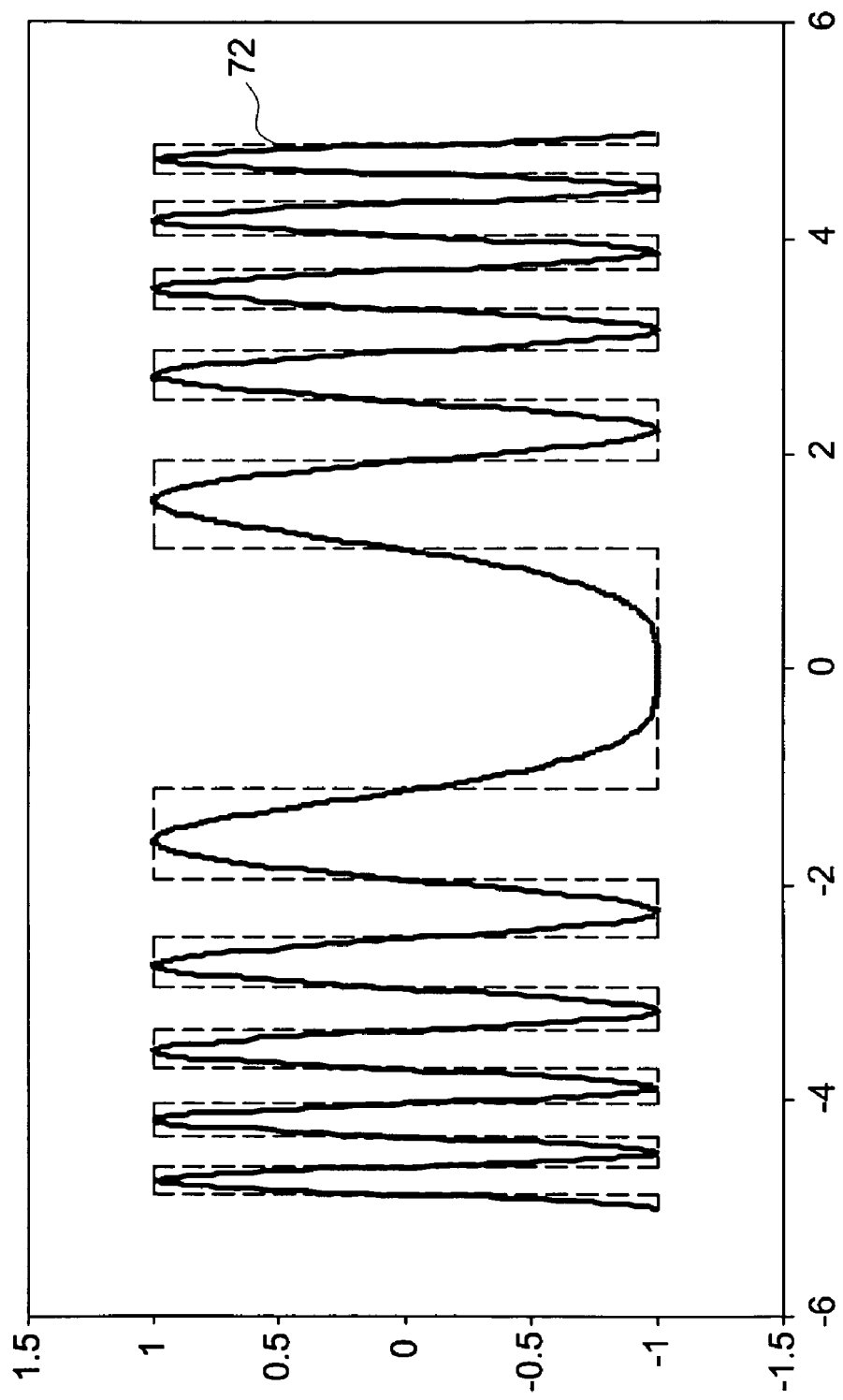
FIG. 5 is a graph illustrates smoothly varying apodization across the transducer.

In another embodiment, the apodization values comprise real numbers ranging from −1 to +1. Constructive regions on the transducer array are assigned negative apodization values and destructive regions on the transducer array are assigned positive apodization values. Regions that contribute strongly toward focusing are assigned apodization values with magnitudes, which are near 1, and regions that contribute weakly toward focusing are assigned apodization values with magnitudes, which are near 0. In this way, the apodization values can smoothly vary across the array, as shown by curve 72 in FIG. 5.

The varying apodization values are achieved by applying different bias voltages using the bias control system 25 across the elevational segments and/or azimuthal segments of the transducer elements of the transducer array 17. Apodization values of zero can effectively be achieved by applying a bias voltage of zero or by interleaving a pair of equal and opposite bias voltages to transducer elements on scale significantly smaller than the typical wavelength of the received ultrasound wave. In a specific embodiment using cMUTs, an apodization value of zero is achieved by applying a sufficiently high bias to cause membrane collapse thus preventing significant motion. The bias voltage is dependent on a geometry of the cMUT. A resistor-divider network can also be used to produce any desired bias voltage for a given element in transducer array 17.

In specific embodiments with capacitive micromachined ultrasound transducers (cMUT) or electrostrictive transducer elements, the polarity as well as the amplitude of the element response to a given excitation voltage (when transmitting) or to a given wavefront (when receiving) is modified by changing the sign and amplitude of its bias voltage. Thus for a one-dimensional cMUT or electrostrictive transducer array with addressable elevational segments, apodization profiles may be realized by applying different bias voltages (in sign and amplitude) to the elevational segments of the transducer. The manner in which the bias voltages and polarities are determined is described in further detail with reference to FIG. 6.

Figure 6:
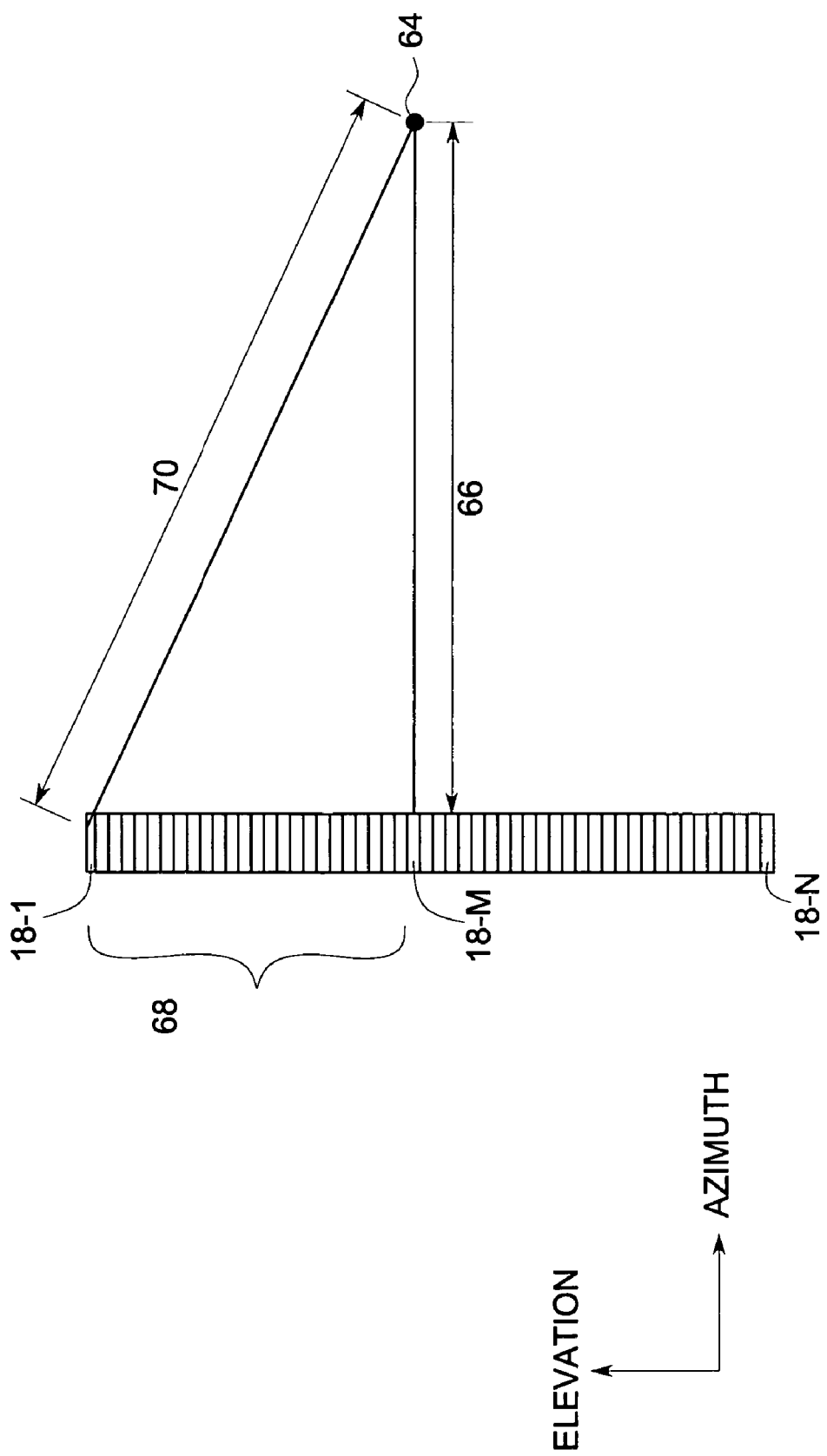
FIG. 6 is a diagrammatic view of a transducer at a distance from the focal point.

FIG. 6 is a diagrammatic view of a transducer element with a focal point at a predetermined distance. Transducer element 17-1 comprises regions 18-1 through 18-N. The Fresnel reference point is at 18-M. The distance 'r' between the Fresnel reference point to the focal point 64 is represented by reference numeral 66. The distance 'y' between the region 18-1 and the Fresnel reference point is 68. The distance 's' between the region 18-1 to the focal point 64 is represented by reference numeral 70. The propagation path length difference 'Δ', between the distances 66 and 70 is determined by the following equation:

$$\Delta \equiv s - r = \sqrt{r^2 + y^2} - r \qquad \text{Equation (1)}$$

In one embodiment, the polarity of bias voltage is dependent on the propagation path length difference. In a specific embodiment, the polarity of the bias voltage is obtained using the following equation:

$$\text{Bias Voltage Sign} = \text{sign}\{\text{mod}[\Delta/\lambda, 1] - \tfrac{1}{2}\} \qquad \text{Equation (2)}$$

where λ is the typical wavelength of the emitted or received ultrasound energy, sign(x)=1 when x>0, sign(x)=0, if x=0 and sign(x)=−1, if x<0, and where mod[n, m] is the modulus operator, i.e., the remainder after division of the n by m.

In another specific embodiment, the polarity of the bias voltage is obtained using the following equation:

$$\text{Bias Voltage Sign} = \text{sign}\{\text{mod}[\Delta/\lambda + \tfrac{1}{4}, 1] - \tfrac{1}{2}\} \qquad \text{Equation (3)}$$

where λ is the typical wavelength of the emitted or received ultrasound energy, sign(x)=1 when x>0, sign(x)=0, if x=0 and sign(x)=−1, if x<0, and where mod[n, m] is the modulus operator, i.e., the remainder after division of the n by m.

Figure 7:
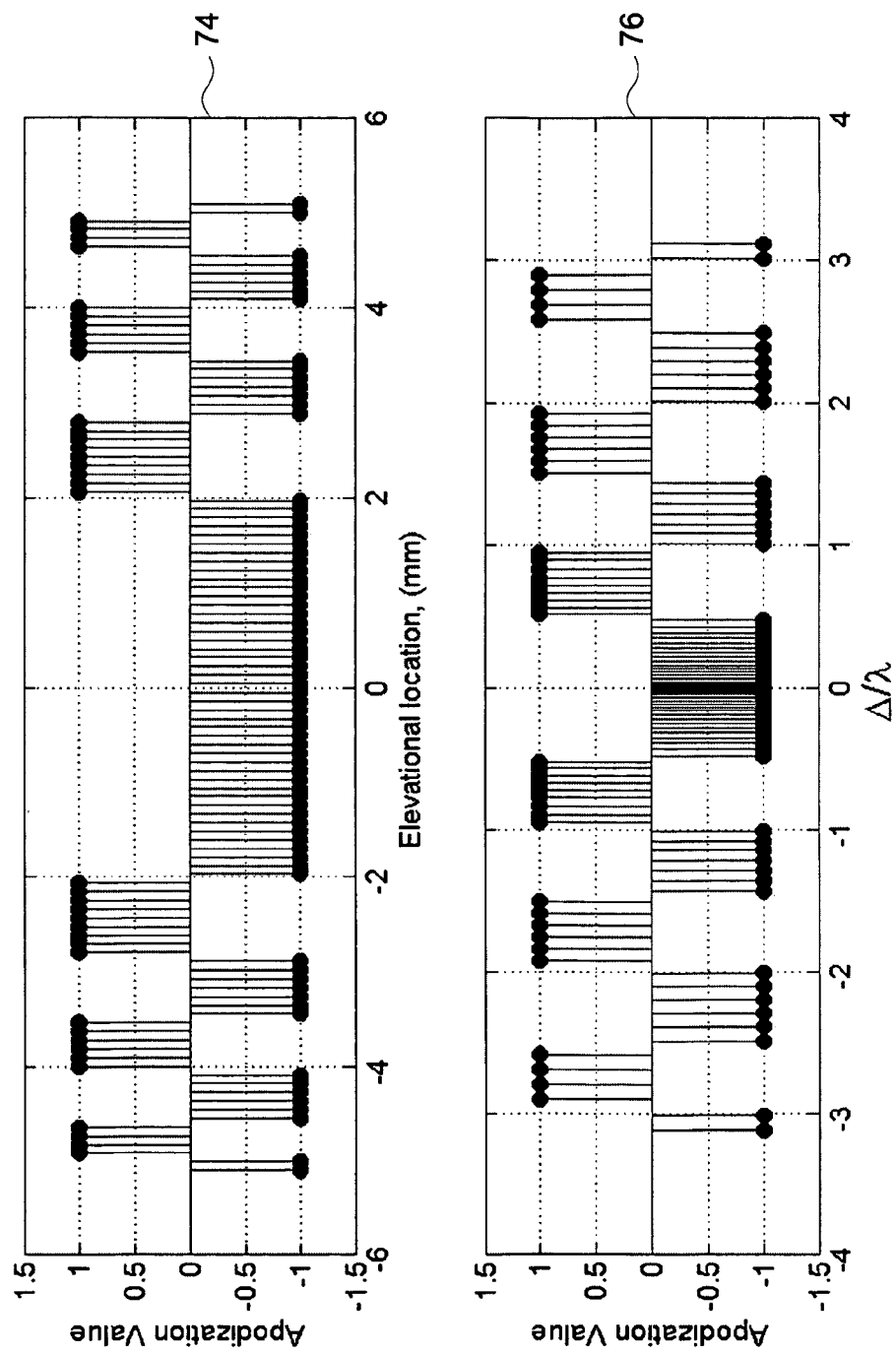
FIG. 7 is an exemplary apodization profile applied to transducer in prior art.

FIG. 7 is an exemplary apodization profile implemented for an ultrasound system according to prior art. In this example, the apodization profile is applied along the elevation dimension. The graph represented by reference numeral 74 shows an exemplary apodization profile containing values restricted to −1 and +1 and calculated using Equation 2 using the value λ=0.205 mm. The elevational height of the transducer is 10.3 mm and is divided into 112 regions. The Fresnel reference point for the profile is at the transducer elevational location 0 mm. The distance from the array to the focus point is 20 mm. The filled circles represent the apodization value at each elevation location. The apodization value is −1 in the constructive regions of the array and +1 in the destructive regions of the array. The graph represented by reference numeral 76 indicates the value of Δ/λ for each elevation location in 74 and the corresponding apodization value calculated using Equation 2.

Figure 8:
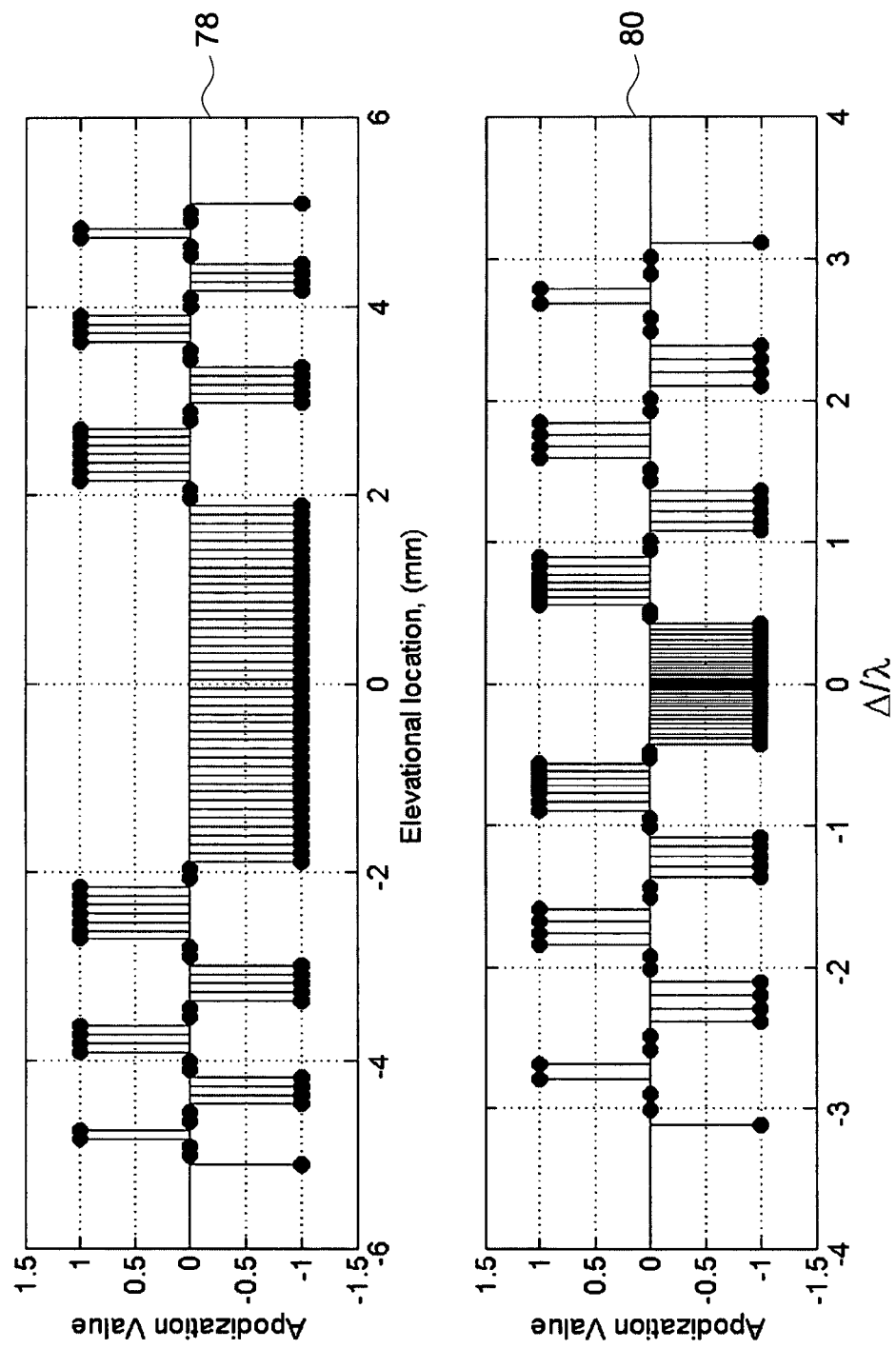
FIG. 8 is an exemplary apodization profile applied to transducer according to one aspect of the present invention.

FIG. 8 is an exemplary apodization profile implemented for an ultrasound system according one aspect of the invention. The graph represented by 78 is an exemplary apodization profile that comprises values −1, 0 and 1 and is applied to transducer elements along the elevation dimension. In the embodiment, an apodization value of −1 is applied to constructive regions, +1 is applied to destructive regions and 0 is applied to transition regions. The graph represented by reference numeral 80 indicates the value of Δ/λ for each elevation location in 78 and the corresponding apodization value.

Figure 9:
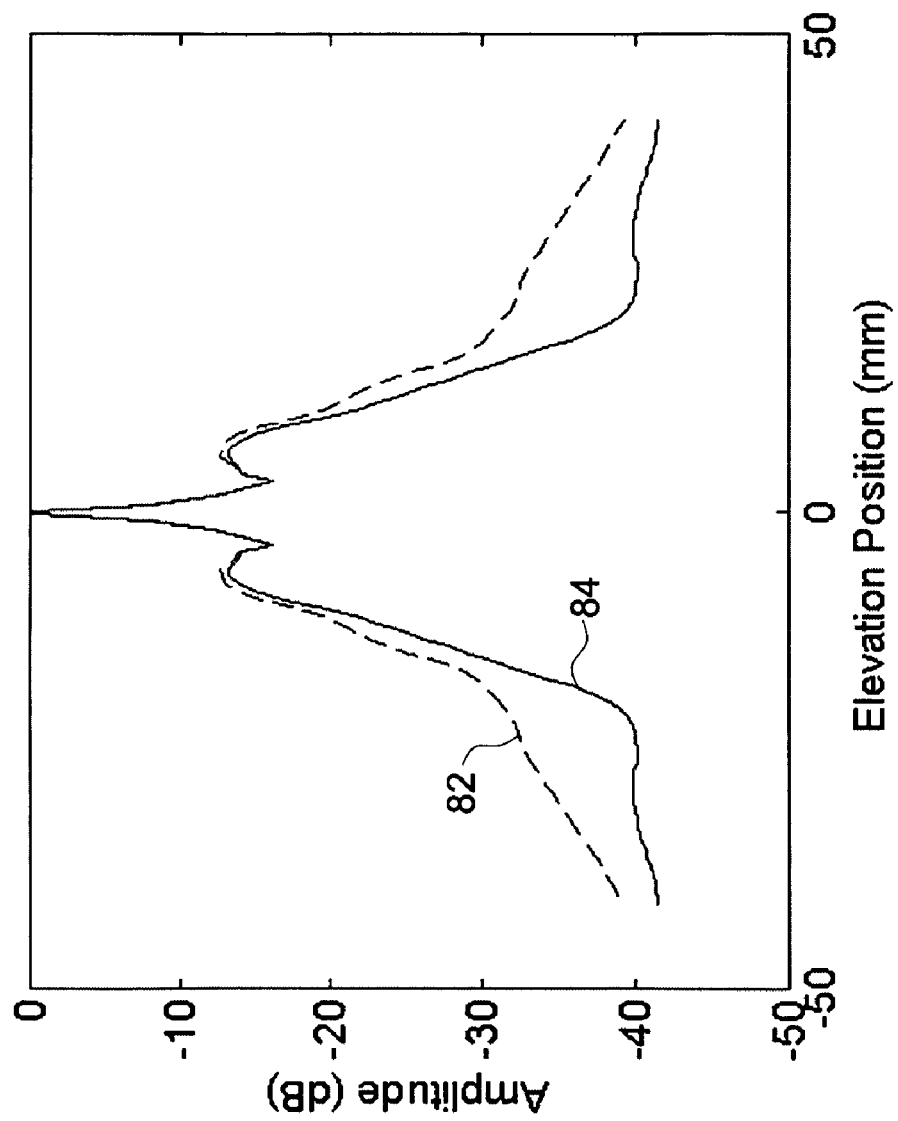
FIG. 9 is a graphical view illustrating a comparison of a relative amplitude (on a logarithmic scale) of the emitted ultrasound energy at the focus of the array when the apodization profiles of FIG. 6 and FIG. 7 are applied.

FIG. 9 is a graphical view of a relative amplitude (on a logarithmic scale) of the emitted ultrasound energy at the focus of the array. The relative amplitude is shown as a function of the elevational position at the focus of the array, which is at a depth of 20 mm, and 0 mm in elevation. Line 82 illustrates the relative amplitude using the prior art apodization profile shown in FIG. 7. Line 84 illustrates the decreased sidelobe levels when the apodization profile of FIG. 8 is applied to the transducer array.

Figure 10:
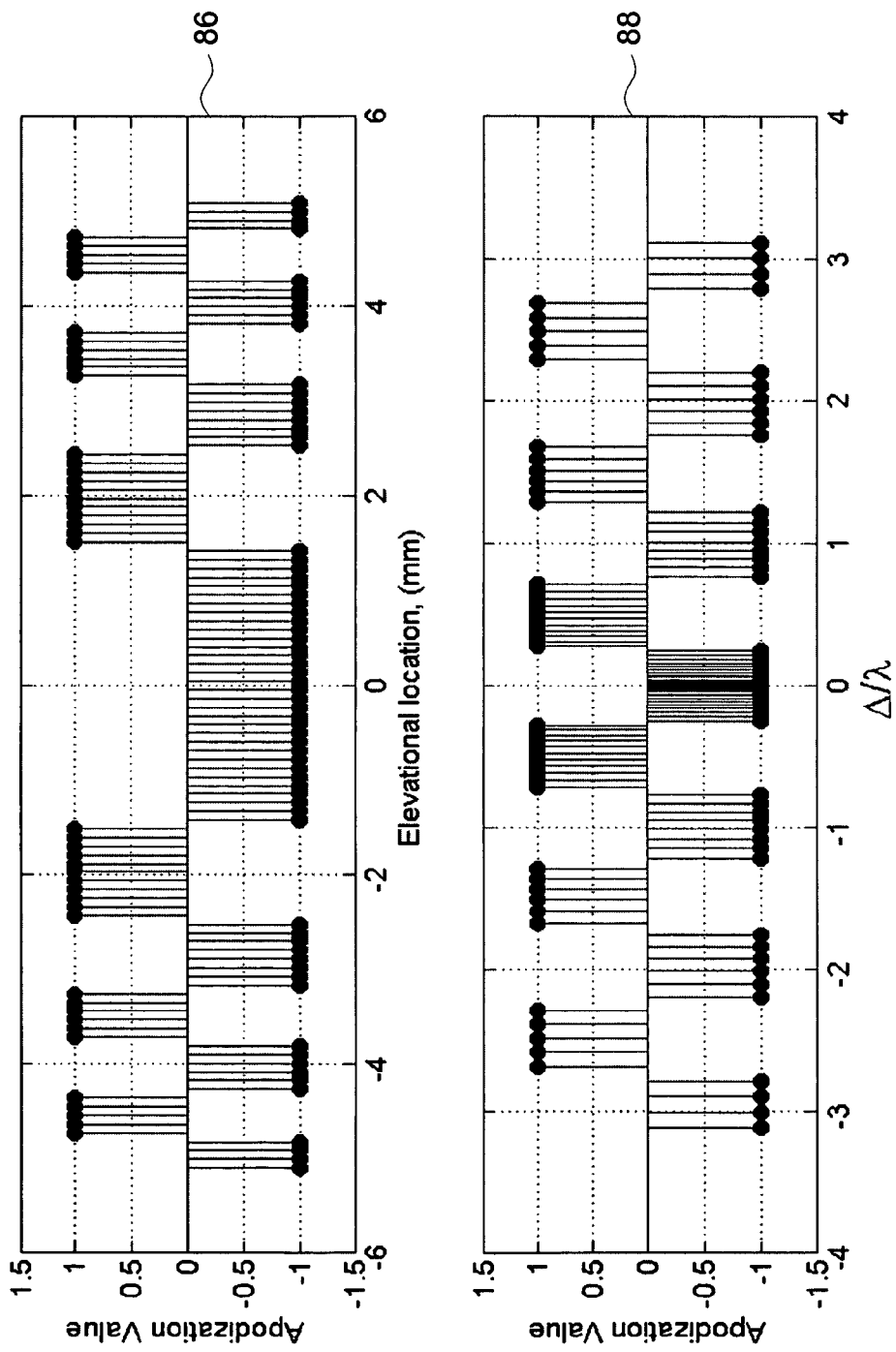
FIG. 10 is an exemplary apodization profile applied to transducer array in prior art.

FIG. 10 is an exemplary apodization profile implemented for an ultrasound system according to prior art. The graph represented by reference numeral 86 shows an exemplary apodization profile containing values restricted to −1 and +1 and calculated using Equation 3. The graph represented by reference numeral 88 shows the values of Δ/λ for each elevation location in 86 and the corresponding apodization value.

Figure 11:
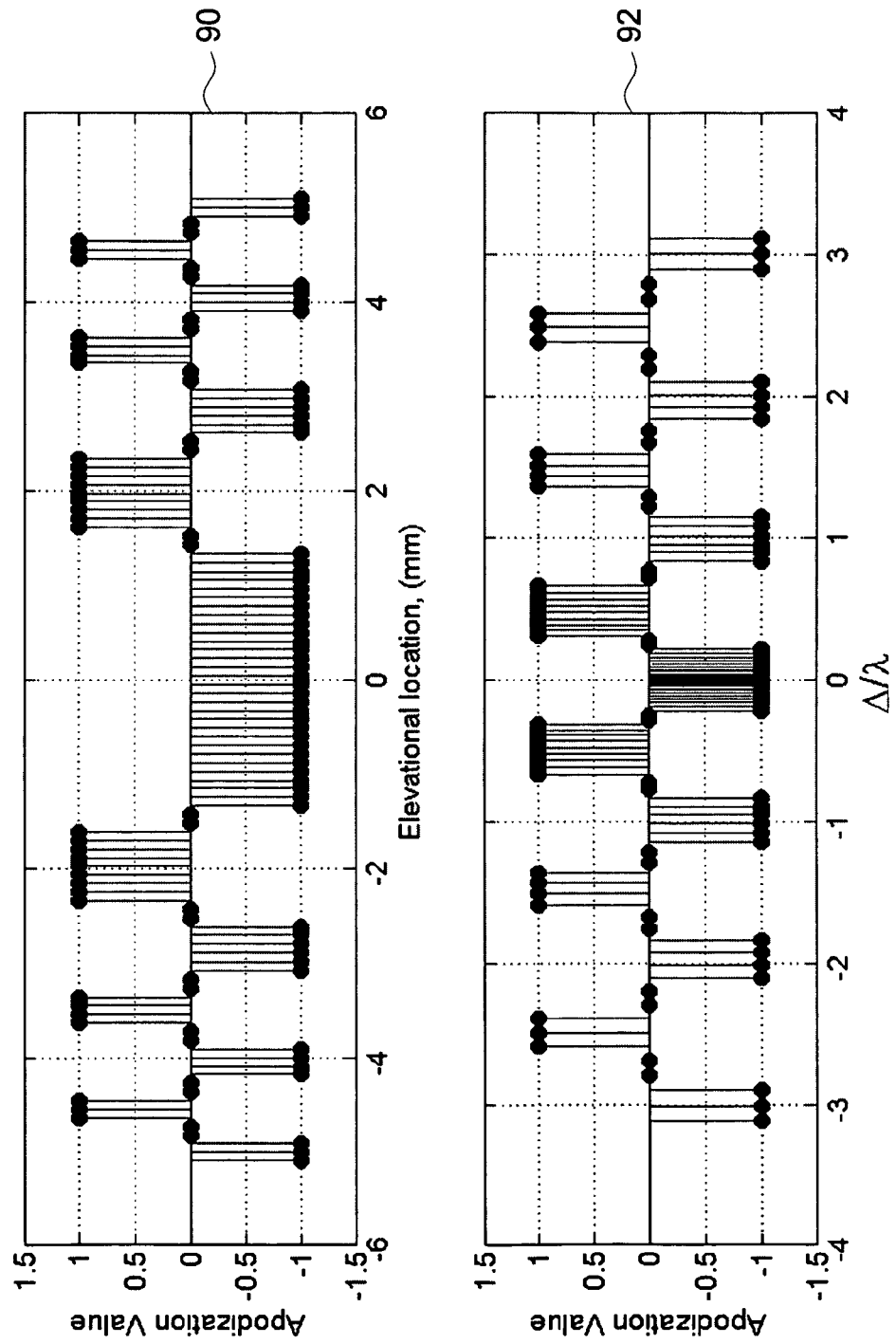
FIG. 11 is an exemplary apodization profile applied to transducer array according to another aspect of the present invention.

FIG. 11 is an exemplary apodization profile implemented for an ultrasound system according one aspect of the invention. The graph represented by 90 is an exemplary apodization profile that comprises values −1, 0 and 1 and is applied to transducer elements along the elevation dimension and calculated using equation 3. The value of zero is applied to transition regions, which lie between constructive regions and destructive regions. The graph represented by reference numeral 92 shows the values of Δ/λ for each elevation location in 90 and the corresponding apodization value.

Figure 12:
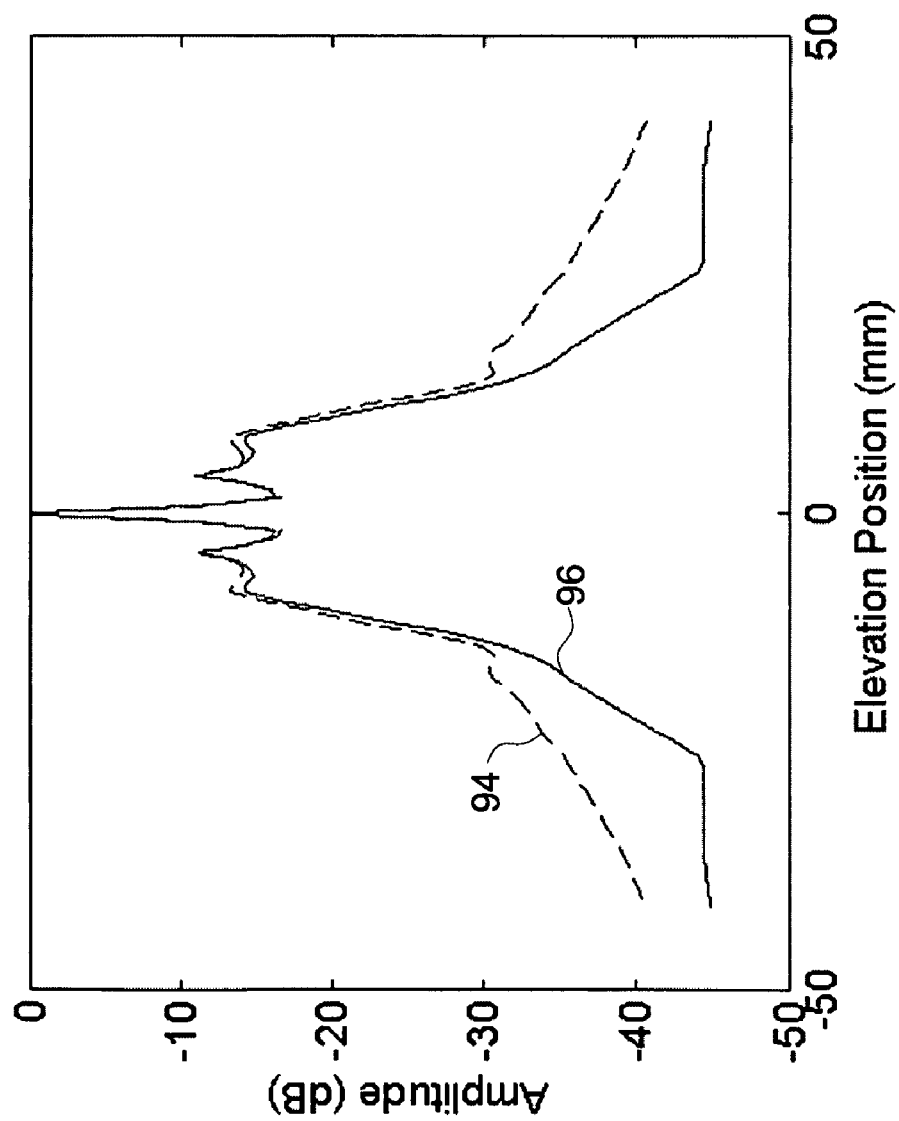
FIG. 12 is a graphical view illustrating a comparison of a relative amplitude (on a logarithmic scale) of the emitted ultrasound energy at the focus of the array when the apodization profiles of FIG. 10 and FIG. 11 are applied.

FIG. 12 is a graphical view of a relative amplitude (on a logarithmic scale) of the emitted ultrasound energy at the focus of the array. The graph compares the relative amplitude of the emitted ultrasound energy using the apodization profiles shown in FIGS. 10 and 11. The sidelobe levels 96 obtained using the apodization profile shown in FIG. 11 are clearly lower than the sidelobe levels 94 obtained using the apodization profile shown in FIG. 10.

The above described invention has various advantages including the ability to improve focusing capability with Fresnel zone imaging methods using minimal modifications to system requirements and resulting in improved resolution for three-dimensional imaging, improved contrast resolution for two-dimensional imaging using Fresnel zone imaging methods.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for Fresnel zone imaging, the method comprising:
    identifying a plurality of constructive regions, a plurality of destructive regions, and a plurality of transition regions in a transducer element which includes at least one MUT; and
    applying an apodization profile to the plurality of regions, wherein the apodization profile comprises apodization values for each constructive region, destructive region, and transition region, wherein the apodization values include zero, wherein the apodization value for the plurality of transition regions is zero, wherein a high bias voltage is applied to at least one said MUT to obtain at least one said apodization value of zero.

2. The method of claim 1, wherein the apodization values comprise real numbers −1, 0 and +1.

3. The method of claim 1, wherein the apodization values comprise continuously varying real numbers from −1 to +1 inclusive.

4. The method of claim 1, wherein the transducer element comprises a transducer array.

5. The method of claim 4, wherein the transducer array comprises micromachined ultrasound transducers (MUT).

6. The method of claim 5, wherein each apodization value in the apodization profile corresponds to a bias voltage for a respective MUT.

7. The method of claim 6, further comprising applying the bias voltages to the MUT.

8. The method of claim 1, wherein the apodization value of zero is produced by rapid alternation of apodization values of equal and opposite signs.

9. The method of claim 1, wherein the imaging method is adapted for use in at least one of an ultrasound imaging system, a radar system, a sonar system and an optical system.

* * * * *